US00PP34213P2

(12) United States Plant Patent
Robinson et al.

(10) Patent No.: US PP34,213 P2
(45) Date of Patent: May 10, 2022

(54) ***CERCIS* PLANT NAMED 'RNI-RCC3'**

(50) Latin Name: *Cercis canadensis*
Varietal Denomination: RNI-RCC3

(71) Applicant: Robinson Nursery, Inc., McMinnville, OR (US)

(72) Inventors: Joshua Ryan Robinson, McMinnville, OR (US); Christopher Lee Robinson, McMinnville, OR (US)

(73) Assignee: Robinson Nursery, Inc., McMinnville, OR (US)

( * ) Notice: Subject to any disclaimer, the term of this patent is extended or adjusted under 35 U.S.C. 154(b) by 0 days.

(21) Appl. No.: 17/375,276

(22) Filed: Jul. 14, 2021

(51) Int. Cl.
*A01H 5/02* (2018.01)
*A01H 6/00* (2018.01)

(52) U.S. Cl.
USPC ..... Plt./216
CPC ..... *A01H 6/00* (2018.05)

(58) Field of Classification Search
USPC ..... Plt./216
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct variety of *Cercis* plant named 'RNI-RCC3' is disclosed, characterized by distinctive, dark purple foliage that retains its color in heat. Plants are very straight and upright, with exceptional vigor. The new variety is a *Cercis*, normally used for outdoor ornamental purposes.

3 Drawing Sheets

Latin name of the genus and species: *Cercis canadensis*.
Variety denomination: 'RNI-RCC3'.

BACKGROUND OF THE INVENTION

The new *Cercis* cultivar is a product of a planned breeding program conducted by the inventor in Wisconsin. The objective of the breeding program was to develop a highly vigorous plant with dark purple, persistent foliage color, and a straight, upright habit. The new variety is the result of open pollination occurring during the Summer of 2015.

The new variety was developed through an open pollination program in which seed was bulk collected from various unnamed varieties of *Cercis canadensis*. As the seed was bulk collected and resulted from open-pollination, both parents cannot be accurately identified. The new variety was selected on May 5, 2017, by the inventor in a group of seedlings resulting from the open pollination, in a commercial nursery in Oregon.

Asexual reproduction of the new cultivar has been performed by budding. This was first performed at a commercial nursery in McMinnville, Oreg., Aug. 15, 2018, and has shown that the unique features of this cultivar are stable and reproduced true to type in multiple successive generations.

SUMMARY OF THE INVENTION

The cultivar 'RNI-RCC3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RNI-RCC3' These characteristics in combination distinguish 'RNI-RCC3' as a new and distinct *Cercis* cultivar:

1. Dark purple foliage.
2. Retains distinctive foliage color even in heat.

3. Exceptional vigor, reaching 10-12' in one year.
4. Very straight, upright habit.

PARENT COMPARISON

Parent comparisons are unavailable, as both parents are unidentified.

COMMERCIAL COMPARISON

Plants of the new cultivar 'RNI-RCC3' are comparable to the commercial variety *Cercis* 'Forest Pansy', U.S. Plant Pat. No. 2,556. The two *Cercis* varieties are similar in most horticultural characteristics; however, the new variety 'RNI-RCC3' differs in the following:

1. Plants of the new variety grow more vigorously than plants of this comparator.
2. Plants of the new variety have longer internodes than plants of this comparator.
3. Plants of the new variety are taller, with larger calipers than plants of this comparator.
4. Trunks of the new variety are very straight; trunks of this comparator are less straight.
5. Plants of the new variety have darker purple foliage than plants of this comparator.

Plants of the new cultivar 'RNI-RCC3' are comparable to the commercial variety *Cercis* 'JN16', U.S. Plant Pat. No. 28,627. The two *Cercis* varieties are similar in most horticultural characteristics; however, the new variety 'RNI-RCC3' differs in the following:

1. Plants of the new variety have darker purple foliage than plants of this comparator.
2. Plants of the new variety are taller than plants of this comparator.
3. Plants of the new variety have a more upright habit than plants of this comparator.

BRIEF DESCRIPTION OF THE PHOTOGRAPHS

The accompanying photograph in FIG. 1 illustrates flowering plants outdoors at approximately 4 years old in McMinnville, Oreg.

Figure 1:
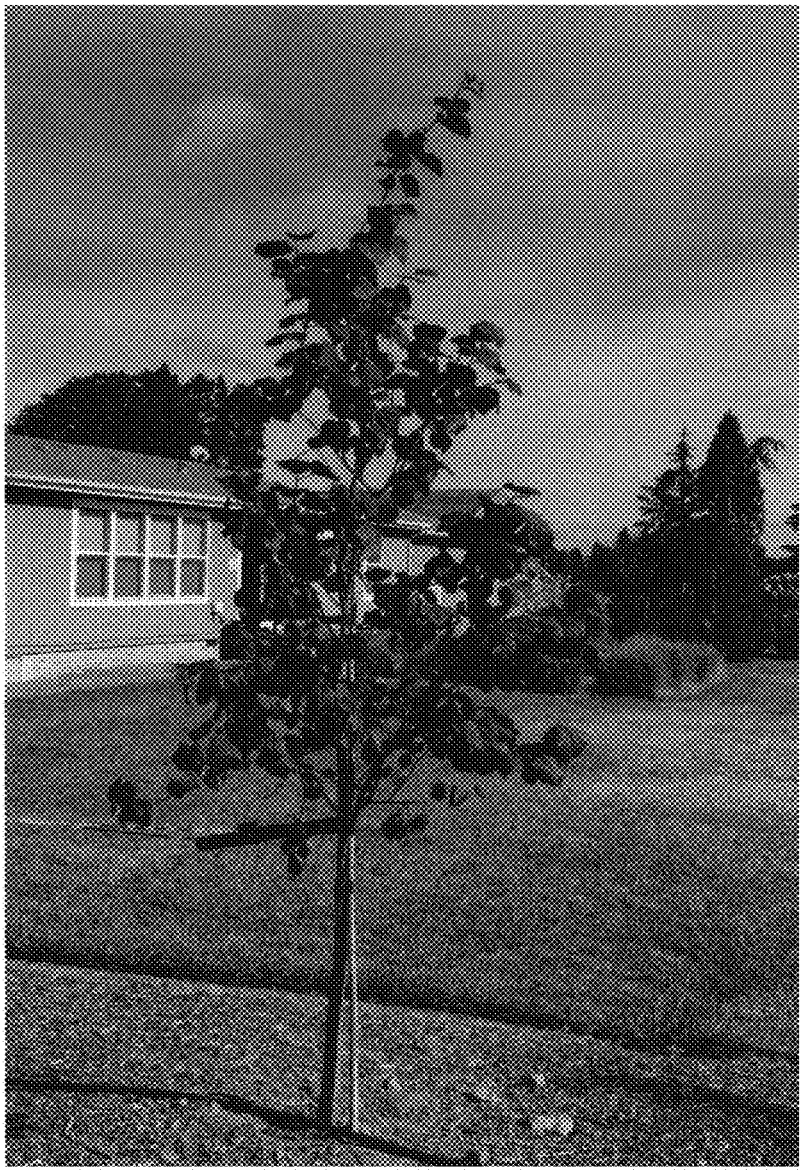
Figure 2:
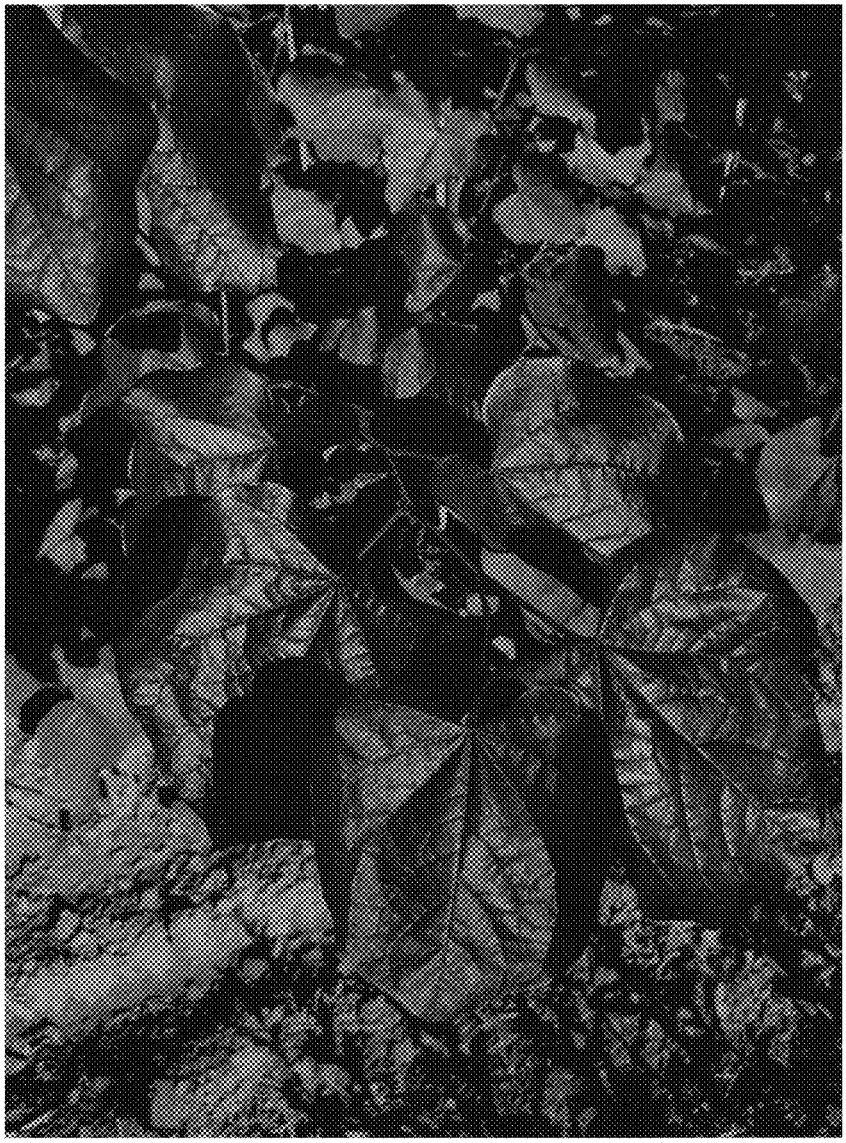
FIG. 2 illustrates in full color a close-up view of the foliage of 'RNI-RCC3'.
Figure 3:
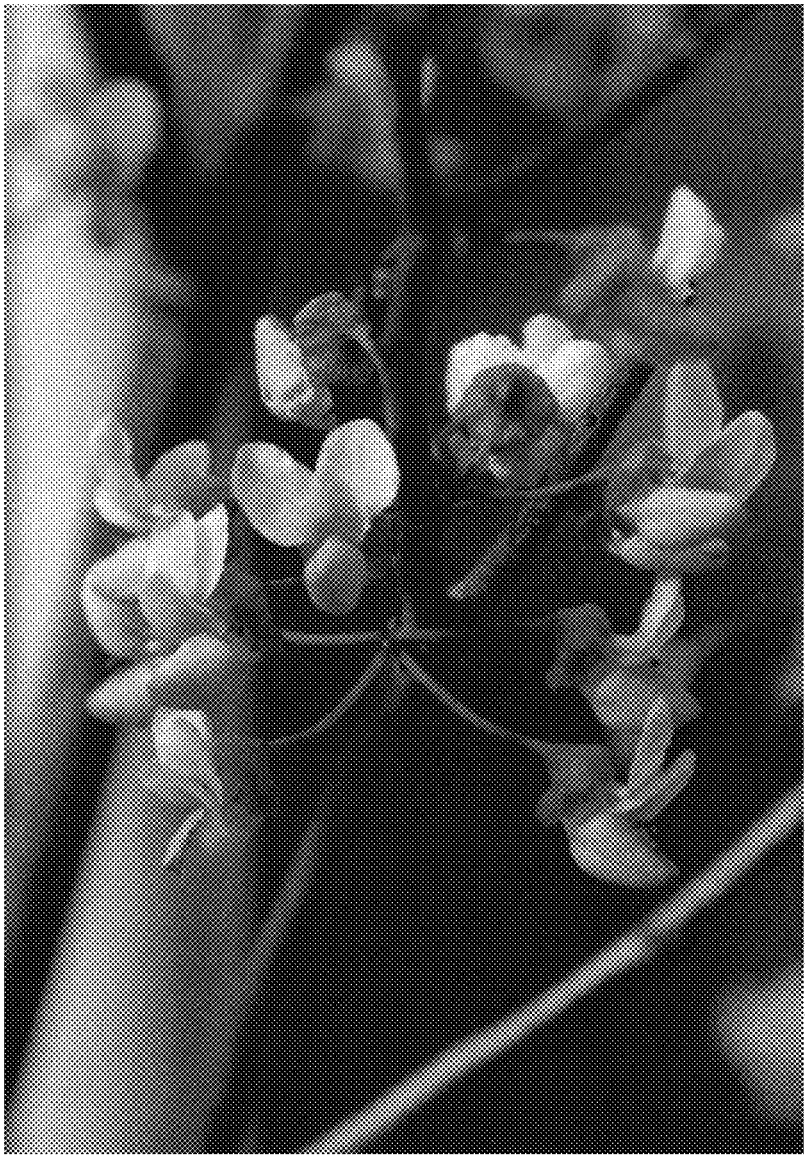
FIG. 3 illustrates a close-up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'RNI-RCC3' plants grown in a poly-house in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Cercis canadensis* 'RNI-RCC3'.

PROPAGATION

Type of propagation typically used: Budding.

Root description: Medium to thick, moderately dense, fleshy, moderately branching. Brown to white in color, not accurately measured with R.H.S. Chart.

PLANT

Age of plant described: 4 years old.
Container size: 10 gallon container.
Overall plant shape: Upright small tree.
Growth habit: Upwards.
Plant spread: 150 cm.
Plant height: 250 cm.
Plant vigor: Vigorous.
Length of primary lateral branches: 75 cm.
Diameter of lateral branches: 7 mm.
Quantity of lateral branches: 12-15.
Aspect angle: Acute.
Internode length: 3.5 cm.
Trunk:
*Diameter*.—About 2 cm measured at approximately 40 cm above soil level at 4 years.
*Color*.—RHS Brown 200B, with Grey-Brown 199B lenticels.
*Texture*.—Somewhat rough with pronounced lenticels.

FOLIAGE

Leaf:
*Arrangement*.—Alternate, single.
*Average length*.—10 cm.
*Average width*.—10 cm.
*Shape of blade*.—Heart-shaped/deltoid.
*Aspect*.—Strong upward fold along center.
*Apex*.—Acuminate.
*Base*.—Cordate.
*Margin*.—Entire.
*Texture of top surface*.—Smooth, soft, glossy.
*Texture of bottom surface*.—Smooth and soft, with pronounced venation.
*Color*.—Young foliage upper side: Near RHS Brown 200A, with some Purple N77A. Young foliage under side: Near RHS Purple N77A. Mature foliage upper side: RHS Yellow-Green 147A, with tinges of Brown 200A. Mature foliage under side: RHS Yellow-Green 148B, with Purple N77A near veins.
*Venation*.—Type: Palmate. Venation color upper side: RHS Yellow-Green 144B. Venation color under side: RHS Greyed-Orange 176B.
*Petiole*.—Length: 3 cm. Diameter: 2 cm. Texture, upper side: Glabrous. Texture, under side: Glabrous. Color, upper side: Near RHS Brown 200A. Color, under side: Near RHS Brown 200A.

FLOWER

Natural flowering season: April and May in Michigan.
Flowers:
*Arrangement*.—Single axillary flowers in small groups of around 4.
*Type*.—Single flowers on axillary branches.
*Diameter*.—13 mm.
*Length*.—14 mm.
*Depth*.—1 cm.
*Aspect*.—Outwards.
*Persistence*.—Self-cleaning.
*Fragrance*.—None.
Petals:
*Arrangement*.—Papilionaceous.
*Number*.—3 upper, 2 lower.
*Shape*.—Pea-like.
*Margin*.—Entire.
*Tip shape*.—Rounded.
*Base shape*.—Attenuate.
*Length*.—Upper: 8 mm. Lower: 1 cm.
*Width*.—Upper: 4 mm. Lower: 4 mm.
*Texture*.—Upper: Smooth. Lower: Smooth.
*Color*.—When opening: Upper surface: Top: RHS Violet 84C; bottom: Red-Purple N74C. Under surface: Top: RHS Violet 84C; bottom: Red-Purple N74B near apex, fading to N74D near base. Fully opened: Upper surface: Top: RHS Violet 84C; bottom: Red-Purple N74C. Under surface: Top: RHS Violet 84C; bottom: Red-Purple N74B near apex, fading to N74D near base.
Bud:
*Shape*.—Papilionaceous.
*Length*.—1 cm.
*Diameter*.—4 mm.
*Color*.—RHS Purple 77C towards the base, to Red-Purple 71C at the top.
Sepals: None.
Calyx:
*Shape*.—Campanulate. Red purple 59A.
*Length*.—4 mm.
*Diameter*.—4 mm.
*Color*.—RHS Red-Purple 59A.
Peduncle:
*Length*.—11 mm.
*Diameter*.—Less than 1 mm.
*Texture*.—Smooth.
*Color*.—RHS Red-Purple 59A.
*Strength*.—Flexible.
Pedicel: None.

REPRODUCTIVE ORGANS

Stamens:
*Number.*—10.
*Filament length.*—5 mm.
*Filament color.*—RHS Red-Purple 59D.
Anthers:
*Shape.*—Globose.
*Length.*—Less than 1 mm.
*Color.*—RHS Violet-Blue N92A.
*Pollen.*—Amount: Moderate. Color: RHS White 155A.
Pistil:
*Number.*—1.
*Length.*—5 mm.
*Style.*—Length: 7 mm. Color: RHS Red-Purple 59A.
Stigma:
*Shape.*—Round.
*Color.*—RHS Red-Purple 59A.

OTHER CHARACTERISTICS

Fruits and seeds: Not observed to date.
Disease/pest resistance: Neither resistance nor susceptibility to normal diseases and pests of *Cercis* observed.
Temperature range: USDA ZONES 5 TO 9.

What is claimed is:

1. A new and distinct cultivar of *Cercis* plant named 'RNI-RCC3' as herein illustrated and described.

* * * * *